US006809816B2

(12) United States Patent
Sharma

(10) Patent No.: US 6,809,816 B2
(45) Date of Patent: Oct. 26, 2004

(54) MEASUREMENT OF FLUORESCENCE DECAY TIMES

(75) Inventor: Shiv Sharma, Little Chalfont (GB)

(73) Assignee: Amersham Biosciences UK Limited, Amersham (GB)

( * ) Notice: Subject to any disclaimer, the term of this patent is extended or adjusted under 35 U.S.C. 154(b) by 52 days.

(21) Appl. No.: 10/381,451

(22) PCT Filed: Sep. 27, 2001

(86) PCT No.: PCT/GB01/04313

§ 371 (c)(1),
(2), (4) Date: Mar. 24, 2003

(87) PCT Pub. No.: WO02/27300

PCT Pub. Date: Apr. 4, 2002

(65) Prior Publication Data

US 2004/0012780 A1 Jan. 22, 2004

(30) Foreign Application Priority Data

Sep. 27, 2000 (GB) .............................................. 0023619

(51) Int. Cl.[7] ............................. G01N 21/64; G01J 3/30
(52) U.S. Cl. ..................... 356/318; 356/317; 250/459.1
(58) Field of Search ............................... 356/317–318, 356/417; 250/458.1–461.2

(56) References Cited

U.S. PATENT DOCUMENTS

| 4,791,310 | A | | 12/1988 | Honig et al. | |
|---|---|---|---|---|---|
| 4,855,930 | A | * | 8/1989 | Chao et al. | 356/318 |
| 4,942,303 | A | * | 7/1990 | Kolber et al. | 250/458.1 |
| 5,061,076 | A | | 10/1991 | Hurley | |
| 5,459,323 | A | * | 10/1995 | Morgan | 250/458.1 |
| 6,201,989 | B1 | * | 3/2001 | Whitehead et al. | 250/461.2 |
| 6,317,207 | B2 | * | 11/2001 | French et al. | 356/318 |
| 6,342,701 | B1 | * | 1/2002 | Kash | 250/458.1 |

FOREIGN PATENT DOCUMENTS

EP     0 296 136     12/1988

OTHER PUBLICATIONS

Li–Qiang, Li, et al. "Single Photon Avalanche Diode for Single Molecule Detection" Review of Scientific Instruments, American Institute of Physics, New York, US vol. 64, No. 6, Jun. 1993 pp. 1524–1529.

Hungerford, G., et al. "Single–Photon Timing Detectors for Fluorescence Lifetime Spectroscopy" Measurement Science and Technology, IOP Publishing, Bristol, Great Britain vol. 7, No. 2, Feb. 1, 1996 pp. 121–135.

* cited by examiner

*Primary Examiner*—F. L. Evans
*Assistant Examiner*—Kara E Geisel
(74) *Attorney, Agent, or Firm*—Royal N. Ronning, Jr.; Stephen G. Ryan; Yonggang Ji

(57) ABSTRACT

Laser pulses from laser head 12 pass through objective lens 16 to a focal spot in sample spot 17. If a pulse hits a fluorophore molecule in the focal spot a fluorescence photon is emitted which is collected by lens 16, reflected by dichroic mirror 15 through filter 20, which blocks photons of other wavelengths, to single photon counting photomultiplier unit 21. On detecting a photon, photomultiplier unit 21 generates an output pulse which is coupled, with a short delay, by pulse controller 30 to driver circuit 24 which causes laser head 12 to generate another laser pulse. Thus the interval between the laser pulses is substantially equal to the time between excitation of, and fluorescence emission by, the fluorophore molecule. Computer 23 coupled to photomultiplier unit 21 and driver circuit 24 determines the decay time by measurement of a number of fluorescence events.

14 Claims, 4 Drawing Sheets

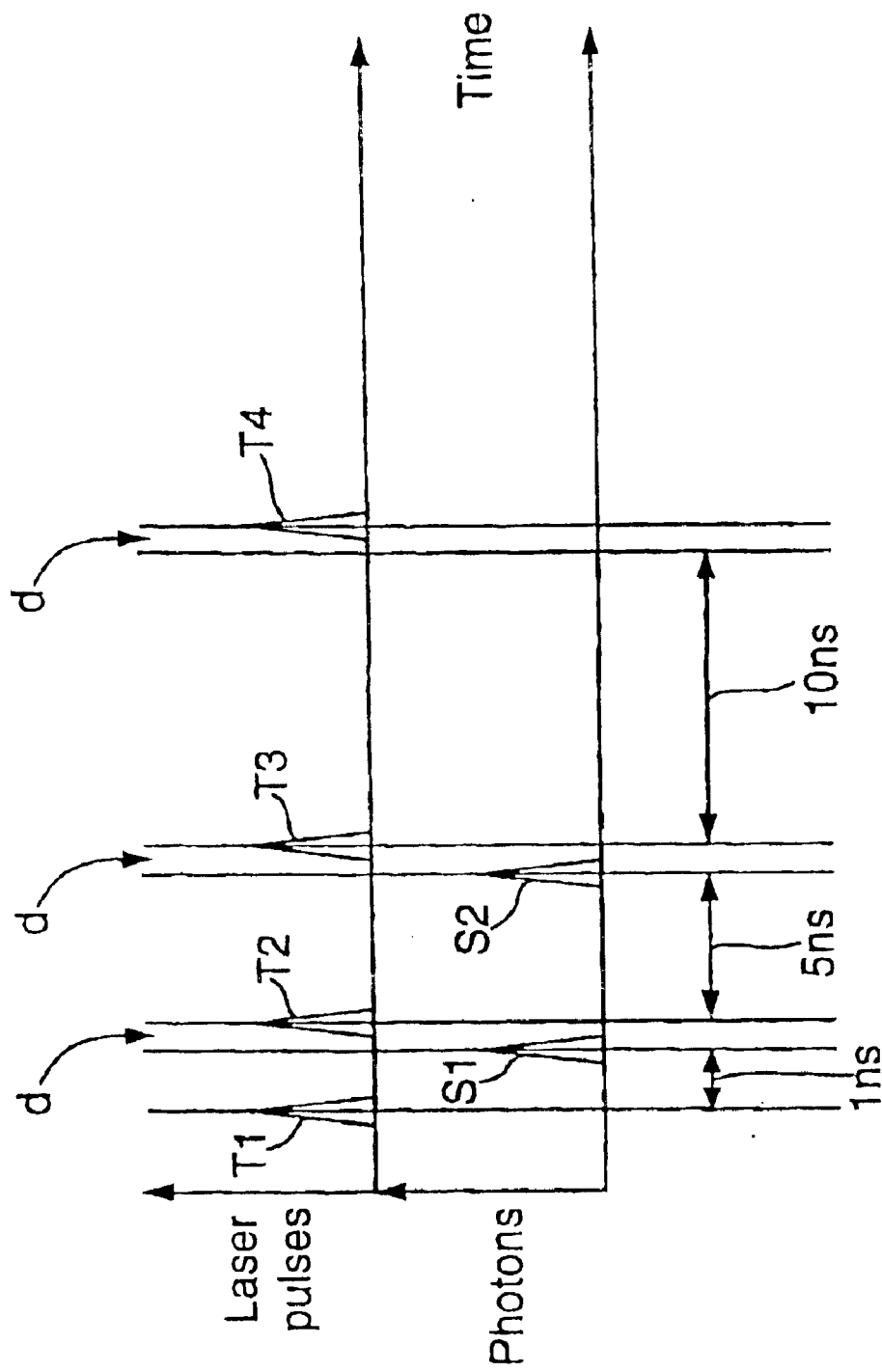

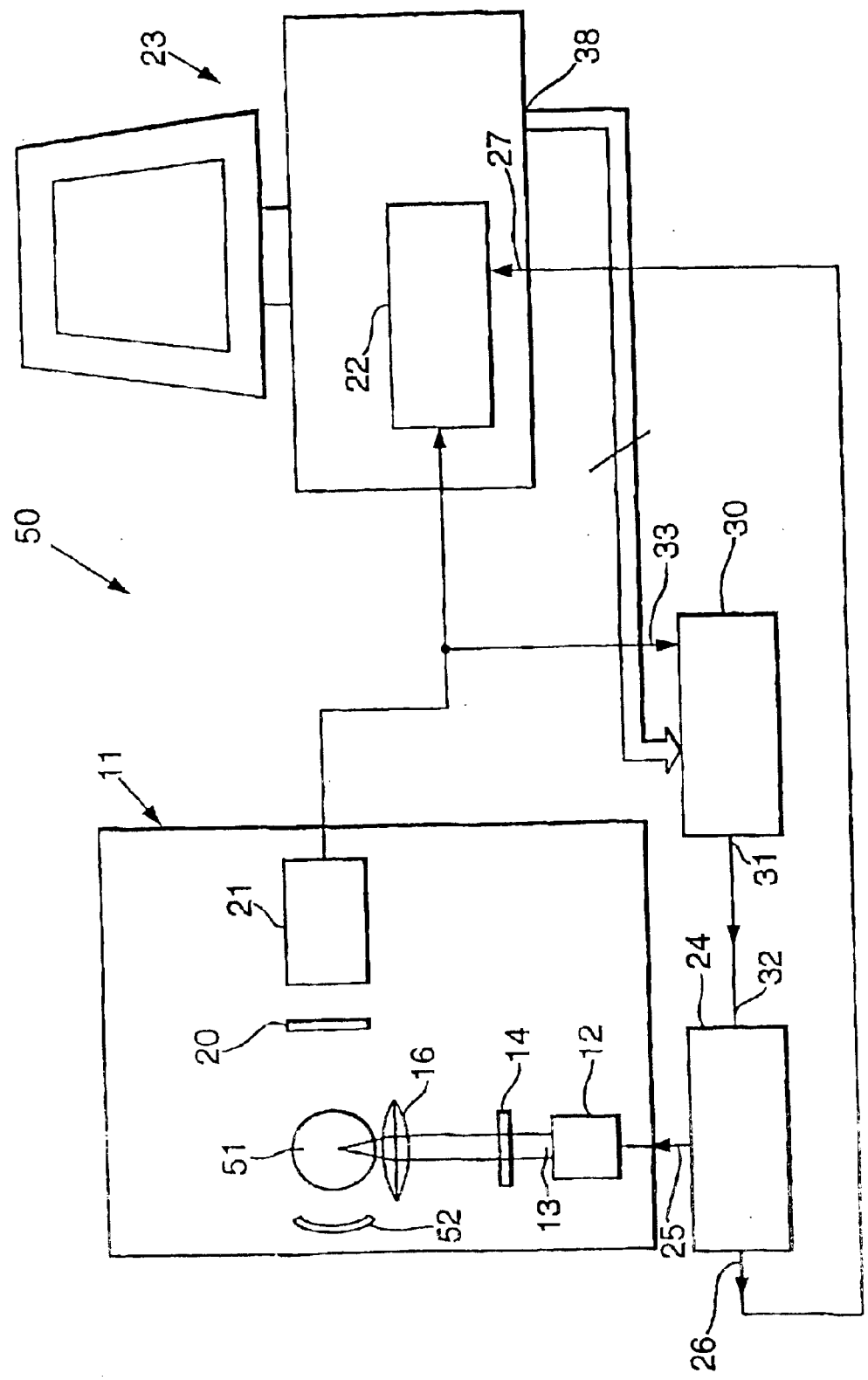

MEASUREMENT OF FLUORESCENCE DECAY TIMES

The present invention relates to a method of and apparatus for measuring a fluorescence decay time.

Since all electrons are normally paired in a molecule, a ground state of a molecule is usually a singlet state. If a molecule in a singlet ground state undergoes a strong initial absorption of a photon to an upper state which is also a singlet state, the excitation energies may be released subsequently by a process which includes the emission of a less energetic photon, i.e. by fluorescence. A more detailed description of the mechanism of fluorescence is given at pages 75 to 78 of "Quanta a handbook of concepts" by P. W. Atkins, Clarendon Press, Oxford, 1974 (ISBN 019 855 494X). In the present specification, an exciting photon may be referred to as light, but it will be understood that the term light is being used in a general sense and is not limited to photons of visible light. For example, the exciting light photons may be infra-red or ultra-violet.

Fluorescent dye molecules are known to be useful for labelling materials, especially biological materials, to enable the labelled materials to be detected in small quantities or distinguished in mixtures. One known technique is that of single molecule detection (SMD) by time correlated single photon counting (TCSPC) in which a single molecule of a fluorophore is repeatedly stimulated to fluorescence by being struck by a regular train of up to 10,000 pulses of light of the appropriate exciting wavelength, measurement of the time between irradiation with an exciting pulse and emission of a fluorescence photon, and determination of the fluorescence decay time from a histogram of the measured times.

A problem of this conventional procedure is that a significantly long time is required to fire the necessary number of exciting pulses at a fluorophore molecule.

Accordingly, the present invention provides a method and apparatus as defined hereinafter in the claims.

In a preferred embodiment of the invention, laser pulses of a selected wavelength are fired from a laser head through an objective lens to a focal spot in a sample spot. If a target fluorophore molecule is present within the focal spot and emits a fluorescence photon which is collected by the objective lens, the fluorescence photon is reflected by a dichroic mirror and passes through a filter, which blocks photons of other wavelengths, to a single photon counting photomultiplier unit. On detecting a fluorescence photon, the photomultiplier unit generates a detection output pulse which is coupled, with a short delay, by a pulse controller to a driver circuit which in response thereto causes the laser head to generate another laser pulse, so that the interval between the laser pulses is substantially equal to the time between excitation of and fluorescence emission by the fluorophore molecule. A personal computer coupled to the photomultiplier unit and the driver circuit determines the fluorescence decay time by measurement of a sufficiently large number of fluorescence events. The sample spot is a disk-like spot of a liquid medium containing a volume density of target fluorophore molecule such that there will most probably be one target fluorphore molecule in the volume of the medium through which a laser pulse passes, the latter volume depending upon the thickness of the sample spot, the diameter of the focal spot, and the numerical aperture of the objective lens. The sample spot is supported by a sample slide. Preferably the sample slide supports a rectangular array of sample spots and is itself secured to a stage movable in steps in two orthogonal directions, to which the rows and columns of the array of sample spots are respectively parallel, so that the array of sample spots can be in effect scanned by the focal spot defined by the objective lens. The personal computer controls movement of the stage and sets a maximum N for the number of laser pulses fired at the slide when held stationary, the stage being moved one step or from the end of one scan line to the beginning of a next scan line on completion of N firings of the laser head. The pulse controller includes a resettable clock circuit which starts running each time it is reset by a detection output pulse from the photomultiplier unit, and only produces an output pulse if it runs to the end of a preset cycling time before the next detection output pulse occurs. Such generation of an output pulse by the resettable clock circuit results in the laser head being caused, after the aforementioned short delay, to fire another laser pulse at the sample slide, and in resetting of the clock circuit. Hence if the firing of a laser pulse fails to result in detection of a fluorescence photon, a subsequent laser pulse is fired after a preset length of time. The preset length of time is preferably controllable by writing a binary number, corresponding to the desired length of time, from a parallel port of the personal computer to a binary register in the clock circuit.

In another preferred embodiment of the invention, the array of sample spots on the slide and the computer controlled stage are replaced by a cuvette filled with liquid sample medium, and a confocal reflector arrangement is employed to direct a large proportion of emitted fluorescence photons into the photomultiplier unit, the focal spot of the objective lens being disposed within the cuvette.

Other preferred features are defined in the dependent claims hereinafter, to which reference should now be made.

The invention will now be described by way of example with reference to the accompanying drawings in which:

FIG. 4 is a graphical representation of timing of laser pulses and single photon detections by a photomultiplier unit included in the apparatus of FIG. 1; and FIG. 5 is a schematic diagram of a second apparatus embodying the invention.

Figure 1:
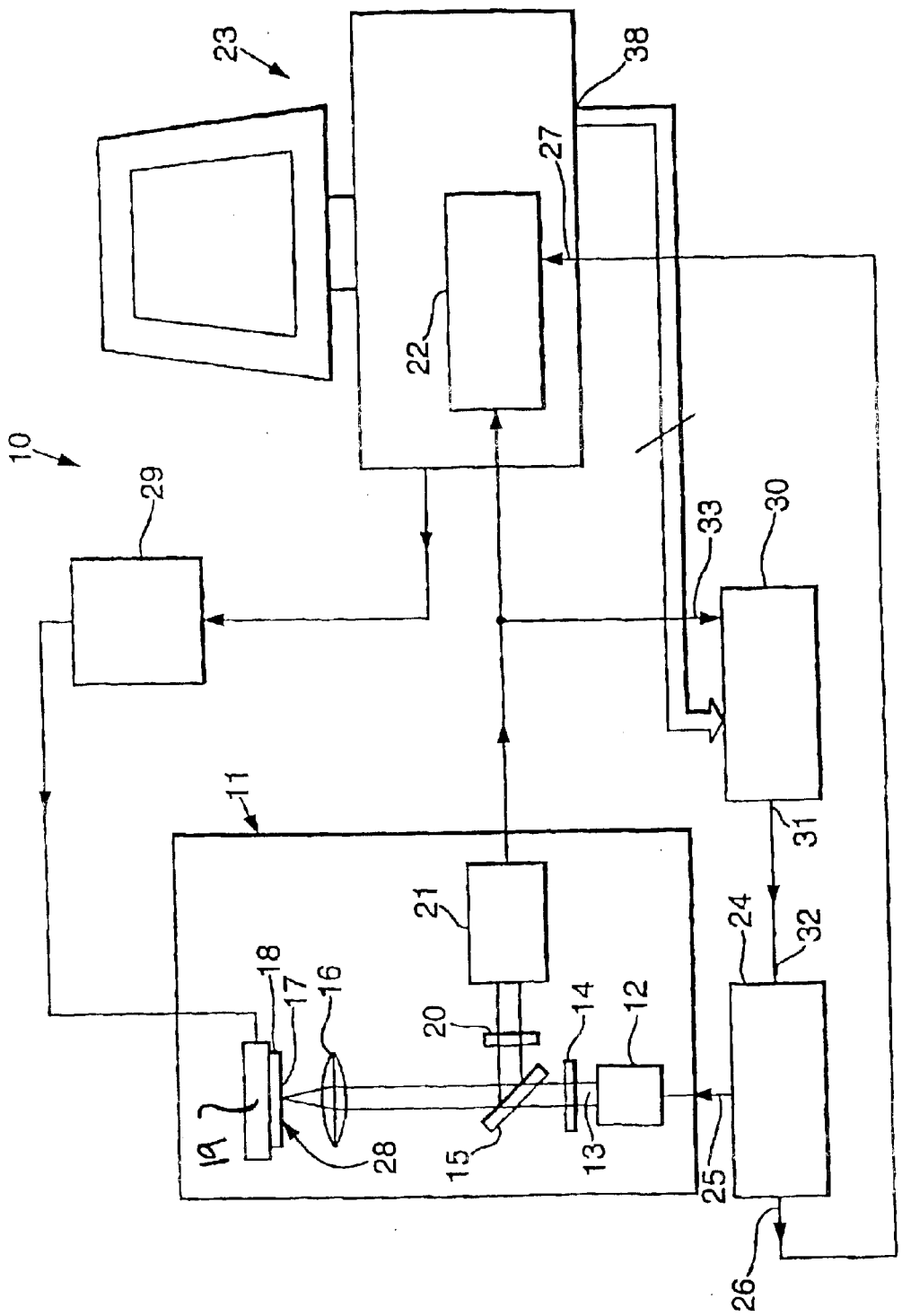
FIG. 1 is a schematic diagram of a first apparatus embodying the invention.

FIG. 1 is a schematic diagram of a first example of an apparatus 10 embodying the invention. The apparatus 10 includes a light box 11 painted matt black on its inside surfaces to absorb any photons which strike those surfaces. Within the light box 11 a laser head 12 is arranged to direct, as a parallel beam 13, light pulses through a first filter 14, a dichroic mirror 15, and an objective lens 16 to a focal spot on a sample spot 17 on a sample slide 18 mounted on a horizontal slide stage 19, the beam 13 being directed vertically upwards. The first filter 14 is chosen to limit the light which is focussed by the lens 16 to a narrow band of wavelengths centred substantially on a chosen wavelength produced by the laser head 12. The sample spot 17 is a substantially circular thin disc of a liquid medium containing molecules of a fluorophore. The diameter of the sample spot 17 may be about 200 times the diameter of the focal spot produced by the objective lens 16, the diameter of the focal spot being typically about 1 micron. The volume density of fluorophore molecules in the sample spot is such that a pulse of laser light passing through the focal spot will most probably interact with only one fluorophore molecule. If a fluorophore molecule is stimulated by a laser pulse from the laser head 12, and a fluorescence photon is emitted in a direction that allows it to be collected by the objective lens 16, the fluorescence photon is reflected by the dichroic mirror 15 through a second filter 20 to a photomultiplier unit 21 where reception of the fluorescence photon results in the generation of a shaped electric output pulse which is supplied to a time correlated single photon counting controller (TCSPC) board 22 in a personal computer 23.

It will be appreciated that the pulses of light from the laser head 12 are of a wavelength which excites fluorescence in a molecule of the fluorophore, and that the liquid medium is transparent both to the excitation radiation, i.e. the pulses of light from the laser head 12, and to fluorescence photons emitted by the fluorophore molecules.

Each light pulse from the laser head 12 is triggered by a drive pulse supplied to the laser head 12 by a driver circuit 24, the circuit 24 having a drive pulse output terminal 25 connected to the laser head 12. The driver circuit 24 also has a drive pulse time signal output terminal 26 at which a timing pulse signal is produced concurrently whenever a drive pulse is supplied by the driver circuit 24 to the laser head 12. The drive pulse time signal output terminal 26 is connected to a trigger input terminal 27 of the TCSPC board 22. The board 22 measures the time interval between the occurrence of a timing pulse signal at its trigger input terminal 27 and the occurrence of a subsequent pulse from the photomultiplier unit 21. The TCSPC board 22 takes into account system delays so as to produce a measurement of the time interval T between a laser pulse interacting with a fluorophore molecule and a consequent emission of a fluorescence photon from that molecule. Such operation of the TCSPC board 22 is known to those skilled in the art, and the board 22 may be, for example, a PicoQuant Time Harp 100 board, as supplied by PicoQuant GmbH of Berlin, Germany. The stage 19, and therefore the slide 18 and the sample spot 17, is held stationary while the laser head 12 fires a chosen number, N, of light pulses at the region of the sample spot 17 at which the focal spot is located. The number N is set by the personal computer 23 and is chosen to ensure that a sufficiently large number of the time intervals T can be measured for a histogram of the values of T to be created by the board 22. Typically, the number N is between 100 and 10,000, i.e. the photomultiplier unit 21 may collect between 100 and 10,000 fluorescence photons from one location of the focal spot defined by the lens 16 and the slide 18 whilst the latter is stationary. The number N depends on the particular fluorophore molecule targeted. Software in the personal computer 23 analyses the histogram produced by the board 22 and fits the measurements to a curve. The curve typically has a steep leading edge to a peak value and an exponential decay from the peak value, the curve being of numbers of occurrences as ordinates against values of the time interval T as abscissae. The software further calculates the fluorescence decay time from this curve, the fluorescence decay time being the difference between the value of T at the peak value and the value of T at (1/e) of the peak value. Suitable software is the F900 curve fitting software supplied by Edinburgh Instruments Limited of Edinburgh, Scotland.

The fluorescence decay time, sometimes referred to as the fluorescence lifetime, is a characteristic of the fluorophore molecule and may be used to identify the molecule if not masked by the presence of other fluorophore molecules having indistinguishably close decay lifetimes.

For a number of reasons, the photomultiplier unit 21 will not detect N fluorescence photons corresponding to N laser pulses fired through the focal spot. First, even if there is a fluorophore molecule in the focal spot, a proportion of any fluorescence photons emitted will not be gathered by the objective lens 16, because they are emitted in directions which give them paths that do not reach the lens 16. Second, the molecule may undergo photo bleaching and cease to emit fluorescence photons. Photo bleaching may result from absorption of a laser photon setting the fluorophore molecule in a triplet state in which it remains for a significantly longer time than the state for fluorescence, or from a chemical change in the fluorophore molecule in response to a laser pulse so that the fluorophore molecule in effect ceases to exist. Third, no fluorophore molecule may be present in the focal spot. The curve fitting software therefore treats the result of N laser pulses as indicative of absence of a fluorophore molecule if there are no corresponding fluorescence photons detected by the photomultiplier unit 21 and if the number of corresponding fluorescence photons detected is less than a predetermined threshold number.

Figure 2:
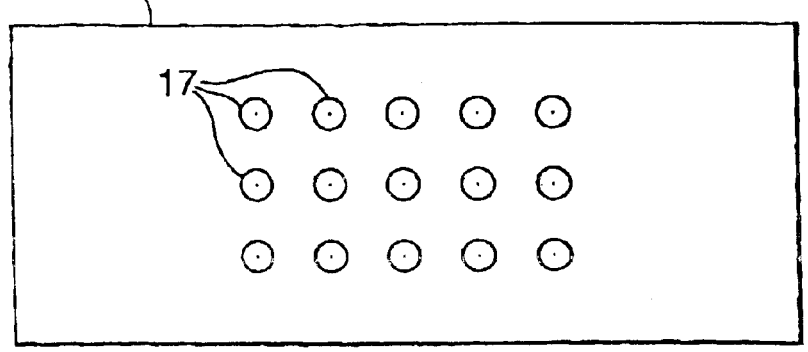
FIG. 2 is a plan view of a sample slide.
Figure 3:
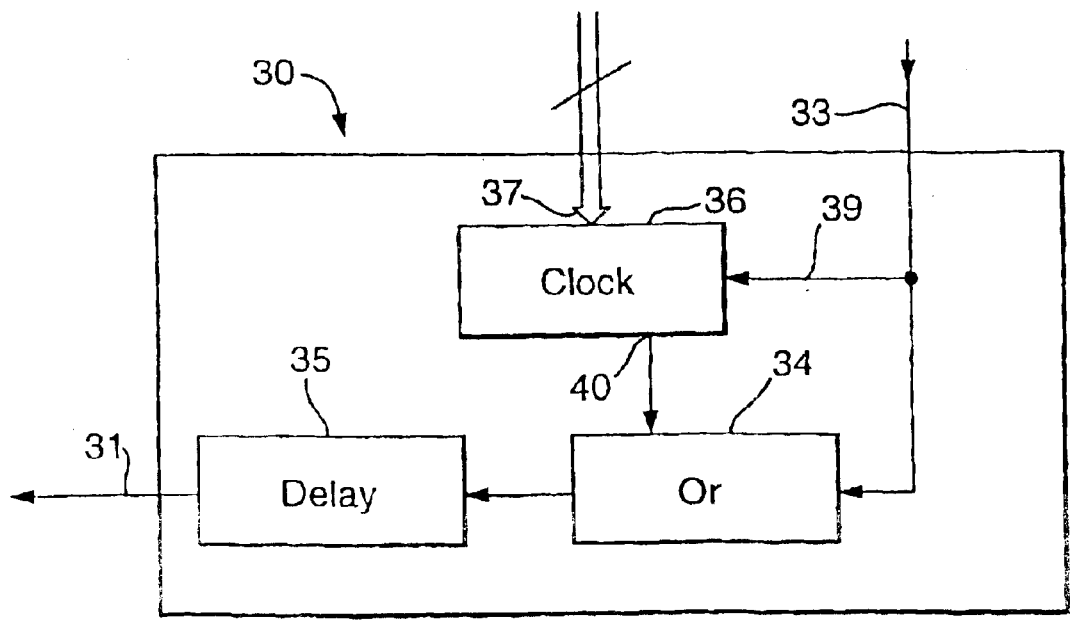
FIG. 3 is a schematic circuit diagram of an electronic pulse controller included in the apparatus of FIG. 1.

FIG. 2 is a plan view of the sample slide 18 and shows that, in this example, there is a rectangular array 28 of 3 rows by 5 columns of sample spots 17. The sample slide stage 19 (FIG. 1) can be moved in an x direction and a y direction, these x and y directions being mutually orthogonal. The slide 18 is secured on the slide stage 19 with the three rows of the rectangular array 28 parallel to the x direction, and the five columns of the rectangular array 28 parallel to the y direction. The slide stage 19 has a drive unit 29 that is controlled by the personal computer 23 and which, in operation, moves the stage 19 in steps in the x direction from x=0 to a fixed maximum value of x, with y=0, returns the stage 19 to x=0, y=0, increments y by one step to y=1 with x=0, and moves the stage 19 in steps in the x direction from x=0 to the fixed maximum value of x, with y=1, returns the stage 19 to x=0, y=1, increments y by one step to y=2 with x=0, and so on so that successive lines parallel to the x direction are scanned stepwise, each line corresponding to a different value of y, and adjacent lines being one step in the y direction apart, until a predetermined maximum value of y is reached and a last line in the x direction is stepped at that maximum value of y. The magnitude of a step in the y direction is equal to the magnitude of a step in the x direction, one step being equal to the diameter of the focal spot defined by the lens 16, so that the focal spot scans a rectangular area. This rectangular area is arranged to cover the whole of the rectangular array 28 and has the same aspect ratio as the rectangular array 28. An example of a suitable slide stage 19 and drive unit 29 is obtainable from Ealing Electro Optics Limited of Watford, Herts, UK.

The computer 23 controls the drive unit 29 in such a manner that the stage 19 is moved by one step or from the end of one line to the beginning of the next line when N firings of the laser head 12 have been completed.

The sample spots 17 on the slide 18 are spaced apart from one another, typically so that the nearest spot in the x or y direction is spaced away by a distance equal to the diameter of a sample spot 17. The laser head 12 continues to fire pulses at each focal spot where the slide 18 dwells between steps whether or not the focal spot lies within a sample spot 17. The second filter 20 prevents any reflected or emitted photons collected by the lens 16 but not originating from a fluorophore molecule from reaching the photomultiplier unit 21.

The photomultiplier unit 21 must be capable of producing an output pulse in response to a single received fluorescence photon. An example of such a photomultiplier unit is the Hamamatsu H5773P-01 which is obtainable from Hamamatsu Photonics of Enfield, Middlesex, UK. The photomultiplier unit 21 typically has a background count of about 200 per second and therefore generates a noise pulse approximately every 5 milliseconds, which is not significant, the fluorescence decay times of fluorophore molecules being of the order of 10 nanoseconds. Other photon counting devices such as those utilizing avalanche photo diodes may be suitable alternatives to such a photomultiplier unit.

For the detection of certain fluorophore molecules it may be necessary to use a laser head 12 which is too large to be mounted within the light box 11, in which case the laser head is mounted outside the light box 11 and directs laser pulses through a window. For example, if it is necessary to use a laser head employing an Argon ion laser, emitting at a wavelength of 488 nanometres, the laser head is mounted outside the light box 11. For a 488 nanometre wavelength Argon ion laser emission, the first filter 14 is an Omega 490DF10, which has a transmission band centred on 490 nanometres, and a band width of 10 nanometres.

If a fluorophore molecule that fluoresces at substantially 515 nanometres is being detected, the second filter 20 is an Omega 515DF10. Such filters have a high rejection of light outside their transmission band, a rejection of 60D (i.e. 1 part in a million) being typical. This rejection ensures that laser photons scattered within the light box 11 cannot pass through the second filter to the photomultiplier unit 21.

The surfaces of the objective lens 16 and other optical surfaces in the optical system between the laser head 12 and the photomultiplier unit 21 are provided with anti-reflection coatings to reduce reflection of the laser light and the fluorescence photons. The numerical aperture of the objective lens 16 is preferably close to unity.

To provide a high numerical aperture, oil immersion of the objective lens 16 may be employed.

If the sample slide 18 provides an optically flat substrate surface for the array 28 of sample spots 17, the focal spot defined by the lens 16 may be positioned in the dimension perpendicular to the array 28 by manual focussing, a manually operable mechanism (not shown) being provided and the laser head 2 being replaced by viewing optics (not shown) for the focussing procedure.

If the sample slide 18 provides an uneven substrate surface for the array 28 of sample spots 17, an automatic focussing system (not shown) is employed. Automatic focussing systems for such purposes are well known to those skilled in the art. For example, an automatic focussing system is described with reference to FIG. 9 of EP-A-0397388. Automatic focussing should be used when the lens 16 provides high magnification.

The laser head 12, the first and second filters 14 and 20, and the dichroic mirror 15 are individually replaceable so that the apparatus 10 can in effect be tuned to suit the absorption and emission wavelengths of specified fluorophore molecules. An example of a replaceable laser head that can be mounted within the light box 11 is the PicoQuant LDH-8-1-152.

Examples of fluorophores molecules, their absorption wavelength and fluorescence emission wavelength in nanometres (nm), and a suitable stimulating laser are given in Table I below.

TABLE I

| Fluorophore | Absorption (nm) | Emission (nm) | Laser |
|---|---|---|---|
| Fluorescein-based molecules | 488 | 510 | 488 nm Argon |
| Cy2 | 489 | 506 | 488 nm Argon |

TABLE I-continued

| Fluorophore | Absorption (nm) | Emission (nm) | Laser |
|---|---|---|---|
| Cy3 | 550 | 570 | 532 nm Frequency doubled YAG |
| Cy5 | 649 | 670 | Diode laser |
| Cy5.5 | 675 | 694 | Diode laser |

The fluorophores Cy2, Cy3, Cy5, and Cy5.5 are cyanine dyes, which are described in U.S. Pat. No. 5,268,486, and are biologically compatible fluorphores characterised by high fluorescence emission and environmental stability, and are available from Amersham Pharmacia Biotech UK Limited, Amersham Place, Little Chalfont, Buckinghamshire, HP7 9NA, United Kingdom.

For sequentially detecting the presence of the four bases in DNA, the following four fluorphores can be used, since they have significantly different fluorescence decay times.

| | |
|---|---|
| Tolnidine | (0.5 nanoseconds) |
| Oxazine 1 | (1.1 nanoseconds) |
| Rhodamin 700 | (2.2 nanoseconds) |
| Oxazine 4 | (3.1 nanoseconds) |

On referring again to FIG. 1 of the accompanying drawings it will be seen that the driver circuit 24 is connected to receive an input from a pulse controller 30. The pulse controller 30 supplies trigger pulses from its output terminal 31 to a trigger pulse input terminal 32 of the driver circuit 24. For the purposes of the present description it is assumed that the driver circuit 24 is a PicoQuant PDL 800. The PicoQuant PDL 800 is constructed to generate drive pulses at its drive pulse output terminal 25 at a selected one of five different pulse repetition frequencies, the highest being 80 megahertz, unless its trigger pulse input terminal 32 is supplied with an externally generated train of trigger pulses with a different pulse repetition frequency. The pulse repetition frequency of 80 megahertz gives a drive pulse interval of 12.5 nanoseconds which, in many instances, is significantly longer than the fluorescence decay time of a fluorophore molecule of interest, such as the four fluorophores listed hereinbefore for detecting DNA bases. However, the circuitry of the PicoQuant PDL 800 is such that it will generate a drive pulse whenever a trigger pulse is supplied to its trigger pulse input terminal 32, and this property is utilized by the present invention, according to which a drive pulse is generated in response to each detection of an emission of a fluorescence photon by the photomultiplier unit 21. It will be appreciated that it is not necessary to use a PicoQuant PDL 800 as the driver circuit 24, since the ability to generate a train of drive pulses at a fixed repetition frequency is not required of the driver circuit 24.

The generation of trigger pulses by the pulse controller 30 will now be described with reference to FIG. 33 of the accompanying drawings.

The controller 30 has a detection signal input terminal 33 which is connected to the output terminal of the photomultiplier unit 21 to receive each output pulse generated by the photomultiplier unit 21 in response to reception of a fluorescence photon. The input terminal 33 is coupled by a two-input OR gate 34 to a delay circuit 35 having an output terminal which serves as the output terminal 31 of the controller 30. Consequently, whenever the photomultiplier unit 21 generates an output pulse, a corresponding pulse appears as a trigger pulse, after a delay, at the output terminal 31.

The controller 30 also includes a resettable, cycling clock circuit 36 having a selectable cycling time which is determined by a binary word applied to a parallel input port 37 of the clock circuit 36 from a parallel output port 38 of the personal computer 23. The clock circuit 36 also has a reset terminal 39 which is connected to the detection signal input terminal 33 to receive each output pulse generated by the photomultiplier unit 21 which therefore serves as a resetting pulse for the clock circuit 36.

In the present example, the cycling time of the clock circuit 36 is set by the personal computer 23 to be 10 nanoseconds.

If the time elapsing from the last reset condition of the clock circuit 36 reaches the cycling time before an output pulse from the photomultiplier unit 21 appears at the reset terminal 39, the clock circuit 36 generates an output pulse at a clock output terminal 40 which is connected to a second input terminal of the OR gate 34. Such a pulse output by the clock circuit 36 is shaped to simulate an output pulse from the photomultiplier unit 21 and is coupled by the OR gate 34 to the delay circuit 35 and therethrough to the controller output terminal 31 where it triggers the driver circuit 24. Consequently, if a laser pulse fails to result in the emission of and collection by the photomultiplier unit 21 of a fluorescence photon, the laser head 12 is fired again at the end of the cycling time of the clock circuit 36, which in the present example is 10 nanoseconds.

Considering as an example the apparatus 10 with the optical components tuned for detection of tolnidine, when there is a tolnidine molecule within the focal spot defined by the lens 16, and its fluorescence photons are being detected sequentially by the photomultiplier unit 21, the laser head 12 will be fired at intervals of the order of 0.5 nanoseconds.

FIG. 4 illustrates the timing of four laser pulses T1, T2, T3, and T4, and their relationship in time to the emission of two fluorescence photons S1 and S2 detected by the photomultiplier unit 21. The photon S1 is illustrated as occurring 1 nanosecond after the first laser pulse T1. The second laser pulse T2 is, in accordance with the invention, generated in response to detection of the first photon S1. There is a short delay d between S1 and T2. Similarly, the second photon occurs 5 nanoseconds after T2, and, after the delay d, the third laser pulse T3 is generated. There is no detection of a fluorescence photon in response to the third laser pulse T3, and consequently at expiry of the cycling time, taken in this example to be 10 nanoseconds, of the clock circuit 36 after the third laser pulse T3 the fourth laser pulse T4 is generated. The delay d, which is attributable principally to the delay circuit 35, may be of the order of or a significant fraction of (as in FIG. 4) 1 nanosecond. The purpose of this delay is to prevent system oscillation.

Pulses generated in and transmitted through the components comprising the photomultiplier unit 21, the pulse controller 30, and the driver circuit 24 are appropriately shaped, as will be understood by those skilled in the art.

It will be appreciated from the foregoing description that the cycling time of the clock circuit 36 may be different from 10 nanoseconds, especially when a fluorophore molecule having a relatively long fluorescence decay time, such as 50 to 100 nanoseconds, is to be detected.

FIG. 5 is a schematic diagram of a second example of an apparatus 50 embodying the invention. The apparatus 50 includes many of the component elements of the apparatus 10, and such component elements are given the same reference numerals in FIG. 5 as they have in FIG. 1. The apparatus 50 differs from the apparatus 10 in omitting the dichroic mirror 15 and having a cuvette 51 instead of the sample slide 18 and the slide stage 19 with its drive unit 29 controlled by the personal computer 23. The focal spot defined by the lens 16 is disposed within the volume defined by the cuvette. The cuvette 51 contains a liquid medium in which there may be fluorophore molecules at such a dilution that it is most probable that there is only one fluorophore molecule within the volume defined by the waist in a focussed laser pulse defined at the focal spot by the lens 16. To maximise the possibility of collection of any fluorescence photon emitted in the waist, a confocal reflector system, one reflector 52 of which is shown, is provided and arranged to ensure that fluorescence photons emitted in many different directions from the waist are directed into the photomultiplier unit 21 and detected thereby.

Other embodiments of the invention may be constructed in which the source of light for exciting a target fluorophore molecule is not a laser. For example, a high pressure flash lamp or a light emitting diode may be used if of suitable wavelength. Use of a laser as the source has the advantage of high intensity.

Furthermore, it will be appreciated from the foregoing description that an electronic circuit which combines the functions of the drive circuit 24 and the pulse controller 30 may replace these two component elements.

With reference again to the apparatus of FIG. 1, it should be noted that the operation of the apparatus can be further speeded up by modifying the software of the personal computer 23 to cause the drive unit 29 to move the slide stage 19 to its next position if no fluorescence photons are detected in response to the firing of a predetermined number n, which is smaller than N, of laser pulses at a stationary point on the slide 18.

What is claimed is:

1. A method of measuring a fluorescence decay time, comprising the steps of:

providing a sample medium containing at least one fluorescence molecule;

directing a sequence of pulses of excitation radiation into the sample medium, the sample medium being transparent to the excitation radiation, the at least one fluorescence molecule being responsive to absorption of such excitation radiation to emit a fluorescence photon, and the sample medium being transparent to such a fluorescence photon;

detecting fluorescence photons emitted from the sample medium in response to the sequence of pulses of excitation radiation;

measuring time intervals each defined by a starting time at which one pulse of the excitation radiation is directed into the sample medium and an end time at which a fluorescence photon is emitted from the sample medium before the occurrence of a next pulse of the excitation radiation in succession in the said sequence; and determining a fluorescence decay time from a plurality of the measured time intervals, characterised by the steps of triggering occurrence of the said next pulse of the excitation radiation in response to detection of the said fluorescence photon which determines the said end time, and limiting the duration of the time between two successive pulses of excitation radiation in the said sequence to a predetermined maximum value.

2. The method of claim 1, wherein each pulse of the excitation radiation is directed through a focal spot arranged to lie within or at a surface of the sample medium.

3. The method of claim 2, further comprising providing relative movement between the focal spot and the sample medium in such a manner that a bounded volume of the sample medium is scanned by the excitation radiation.

4. The method of claim 3, wherein the relative movement is a stepping movement and a sequence of pulses of the excitation radiation is directed into the sample medium between adjacent steps of the movement.

5. The method of claim 4, comprising limiting the sequence of pulses between adjacent steps to a predetermined number N of pulses.

6. The method of claim 5, wherein the predetermined number N is selected based upon the at least one fluorophore molecule in the sample medium, and the sequence of pulses between two adjacent steps is reduced to a small predetermined number n if fewer than a predetermined minimum number of fluorescence photons are detected in response to the sequence of N pulse.

7. An apparatus for measuring fluorescence decay time, comprising:
a source of pulses of excitation radiation;
means for positioning a sample medium containing at least one fluorophore molecule for irradiation by excitation radiation pulses from the said source;
means for detecting fluorescence photons emitted from the sample medium, when present, in response to excitation radiation pulses from the source;
means for measuring time intervals each defined by a starting time at which one pulse is radiated into the sample medium from the source and an end time at which a detected fluorescence photon is emitted from the sample medium before the occurrence of a next pulse of the excitation radiation in succession in the said sequence; and
means for determining a fluorescence decay time from a plurality of the measured time intervals, comprising
means for triggering occurrence of the said next pulse of the excitation radiation in response to detection of the said fluorescence photon which determines the said end time, and
means for limiting the duration of the time between two successive pulses of excitation radiation in the said sequence to a predetermined maximum value.

8. The apparatus of claim 7, further comprising
focussing means for directing each pulse of excitation radiation through a focal spot arranged to lie at a surface of or within the sample medium when present.

9. The apparatus of claim 8, further comprising
means for providing relative movement between the focal spot and the sample medium in such a manner that a bounded volume of the sample medium is scanned by the excitation radiation.

10. The apparatus of claim 9, wherein the relative movement means includes a step movement drive and in that the means for triggering occurrence of the said next pulse is adapted to control the said source in such a manner that a sequence of pulses of the excitation radiation is directed into the sample medium, when present, between adjacent steps of the movement.

11. The apparatus of claim 10, wherein the triggering means is adapted to limit the sequence of pulses between each two adjacent steps to a predetermined number N of pulses.

12. The apparatus of claim 11, wherein the triggering means is adapted to limit the sequence of pulses between two adjacent steps to a smaller predetermined number n than the number N if fewer than a predetermined minimum number of fluorescence photons are detected in response to the sequence of n pulses.

13. The apparatus of claim 7, wherein the means for measuring time intervals includes pulse circuitry coupling the detecting means to means for triggering occurrence of the next pulse of excitation radiation.

14. The apparatus of claim 13, wherein the pulse circuitry includes a resettable clock arranged to activate the said means for causing the source to emit a pulse if the detecting means fails to detect a fluorescence photon within a preset cycling time started in response to the most recent emission of a pulse of excitation radiation by the source.

* * * * *